(12) United States Patent
Munson

(10) Patent No.: US 8,475,508 B2
(45) Date of Patent: Jul. 2, 2013

(54) THERAPEUTIC COOLING SYSTEM

(75) Inventor: Ryan Robert Munson, Tampa, FL (US)

(73) Assignee: Ryan R Munson, Tampa, FL (US)

( * ) Notice: Subject to any disclaimer, the term of this patent is extended or adjusted under 35 U.S.C. 154(b) by 1448 days.

(21) Appl. No.: 12/121,766

(22) Filed: May 15, 2008

(65) Prior Publication Data
US 2009/0287281 A1    Nov. 19, 2009

(51) Int. Cl.
*A61F 7/00*    (2006.01)

(52) U.S. Cl.
USPC ........................................... 607/104

(58) Field of Classification Search
USPC .................. 607/104, 96, 98–99, 102–103
See application file for complete search history.

(56) References Cited

U.S. PATENT DOCUMENTS

| | | | |
|---|---|---|---|
| 3,738,702 A * | 6/1973 | Jacobs | 297/180.15 |
| 5,344,436 A * | 9/1994 | Fontenot et al. | 607/104 |
| 5,372,608 A | 12/1994 | Johnson | |
| 5,562,604 A | 10/1996 | Yablon et al. | |
| 5,737,923 A * | 4/1998 | Gilley et al. | 62/3.7 |
| 6,770,085 B1 | 8/2004 | Munson | |
| 6,964,294 B2 * | 11/2005 | Hendricks et al. | 165/41 |
| 7,191,820 B2 * | 3/2007 | Chou et al. | 165/10 |

\* cited by examiner

*Primary Examiner* — Theodore Stigell
*Assistant Examiner* — Melissa A Snyder

(57) ABSTRACT

A therapeutic cooling system used to remove trapped heat from between a person and an object pressed against the person. Such objects would include: beds, chairs and protective clothing such as body armor. A thin bladder encapsulating a liquid placed between the person and heat trapping object absorbs heat produced by the person. Increased heat transferred to the liquid causes it to expand, become less dense and thus more buoyant than the cooler liquid in the bladder. Convection moves heated liquid upwards towards a thermoelectrically driven cooling unit. When the warmed liquid reaches the cooling unit thermoelectric devices pull heat from the liquid and push it in to a heat sink where is it can expelled from the system. The cooled liquid, now denser, flows back down the bladder by gravity.

20 Claims, 3 Drawing Sheets

THERAPEUTIC COOLING SYSTEM

BACKGROUND OF THE INVENTION

1. Field of the Invention

The invention relates to temperature management systems for people aids and in particular to devices for therapeutically cooling.

2. Description of the Prior Art

The human body is constantly producing heat when metabolizing food. This heat is an import part of bodily function but too much can be detrimental. The body expels extra heat to ambient environment in a variety of ways such as: convection, radiation, and evaporation. All of these ways can be hindered by a thermally insulating material such as the foam padding used in chairs or bedding pressed up against the body trapping in heat. The inability to expel this heat can at first cause the person to become uncomfortable but if the heat continues to build up it could cause severe health effects.

U.S. Pat. No. 5,372,608 to Johnson (1994) is a therapeutic device for chilling a body joint. It is mostly comprised of a flexible container with an inlet port and an outlet port, a tubing system and a reservoir with an inlet and outlet port. When a chilled liquid is added to the reservoir, which is positioned above the flexible container, gravity forces the liquid out of the outlet through the tubing system and in to the flexible container. The flexible container is worn against a persons body part to be chilled where it is warmed up by absorbing heat from the person. The warmed liquid becomes more buoyant and thus flows out of the flexible container up the tubing and back in to the reservoir via its inlet port completing the cycle. This process will continue until the temperature of the chilled liquid rises to the body temperature of the person and can not absorb any more heat energy. This system does not have a means of expelling the heat to the ambient environment.

U.S. Pat. No. 5,562,604 to Yablon (1996) is a portable therapeutic device for treating a patient undergoing hot or cold therapy. This device is comprised of a flexible containment bag means comprising a sealed closed-loop fluid channel containing a liquid, an electromagnetic pumping means, a self-contained source of a therapeutic temperature and microprocessor temperature control. While this device is configured for cooling the flexible containment bag is warn against the person receiving the therapy. Heat is transferred from the person to the bag, which contains the liquid. The liquid receives the heat and rises in temperature. The heated liquid is pumped through the channels using an electromagnetic pump to the self-contained source of therapeutic temperature control. The temperature control unit then removes the heat from the liquid. This portable therapeutic device relies on an electromagnetic pump to move the liquid. Electromagnetic pumps require that the liquid it pumps be a good electrical conductor.

U.S. Pat. No. 6,770,085 to Munson (2004) is a thermal absorbing pad comprising a bladder made of an elastomer material, a thermoelectric cooling unit, a fluid with a boiling point lower than room temperature at 1 atmosphere of pressure and a tube. The bladder and the tube contain the fluid. The tube connects the bladder to the cooling unit and act as a heat pipe to transfer evaporated fluid from the bladder to the cooling unit and condensed fluid from the cooling unit to the bladder. The bladder enclosing a spongy pad and a fluid is where the heat absorption takes place. This heat is transferred to the fluid converting it in to a vapor. The tube conveys the vapor to a cooling unit. A cooling unit than condenses the vapor back into a liquid using a thermoelectric module to remove the heat. This thermal absorbing pad must use a fluid with a boiling point below the body temperature of the person using it in order for it to cool the person.

All of the aforementioned devices have the ability to therapeutically cool a person. Each one has it's own method of accomplishing basically the same thing. Likewise each method has strengths and limitations. The Johnson device is a purely passive device that only cools until it has absorbed all the heat it can handle much like an icepack. It lacks the ability to keep itself cool indefinitely. The Yablon device has the ability to cool the person for as long as the system has power but it has to actively use a pump to move the cooled liquid to the person. The Munson device has the ability to cool the person indefinitely and does not require the use of a pump to actively move the cooling medium to the person. However the cooling medium must be a refrigerant with a boiling point below the temperature of the person. These types of refrigerants are often expensive, have negative impacts on the environment, dangerous and are hard to work with.

SUMMARY OF THE INVENTION

The present invention provides a therapeutic cooling system to remove trapped heat from between a person and an insulative object pressed against the person. The invention provides a pliant bladder to be pressed against the person to be cooled, a liquid used as a transfer medium and a thermoelectric cooling unit to keep the liquid cool. The bladder is a thin liquid filled container with vertical channels to guide the flow of the liquid up and down. Heat from the person being cooled is transferred to the liquid contained in the bladder. The addition of the heat to the liquid causes it to expand and become less dense and thus more buoyant than the cooler liquid. Convection moves heated liquid upwards towards the cooling unit as it is simultaneously replaced by cooler liquid returning by gravity. In the cooling unit thermoelectric coolers remove the heat by pumping it in to a heat sink. The heat sink radiates the heat to ambient air with the help of a fan. The addition of a temperature sensor could be used to regulate the power to the thermoelectric cooling unit keeping the temperature of the liquid to a desired level. Also a flow rate regulator could be used to control the amount of liquid flowing between the bladder and the thermoelectric cooling unit producing a desired temperature in the bladder.

This therapeutic cooling system is a novel device for providing cooling therapy to people for a variety of applications. One such application would be integrated in to a seat back to remove heat from a person sitting in the chair. This would be particularly helpful for handicapped people who often have problems regulating their body temperature. Another application would be between a soldier and a ballistic plate. Trapped heat would be removed from the solider making it more comfortable to wear armor. This therapeutic cooling system is made of very inexpensive and readily available components and materials, has almost no moving parts and contains no harmful chemicals or refrigerants.

DESCRIPTION OF THE PREFERRED EMBODIMENT

Figure 1:
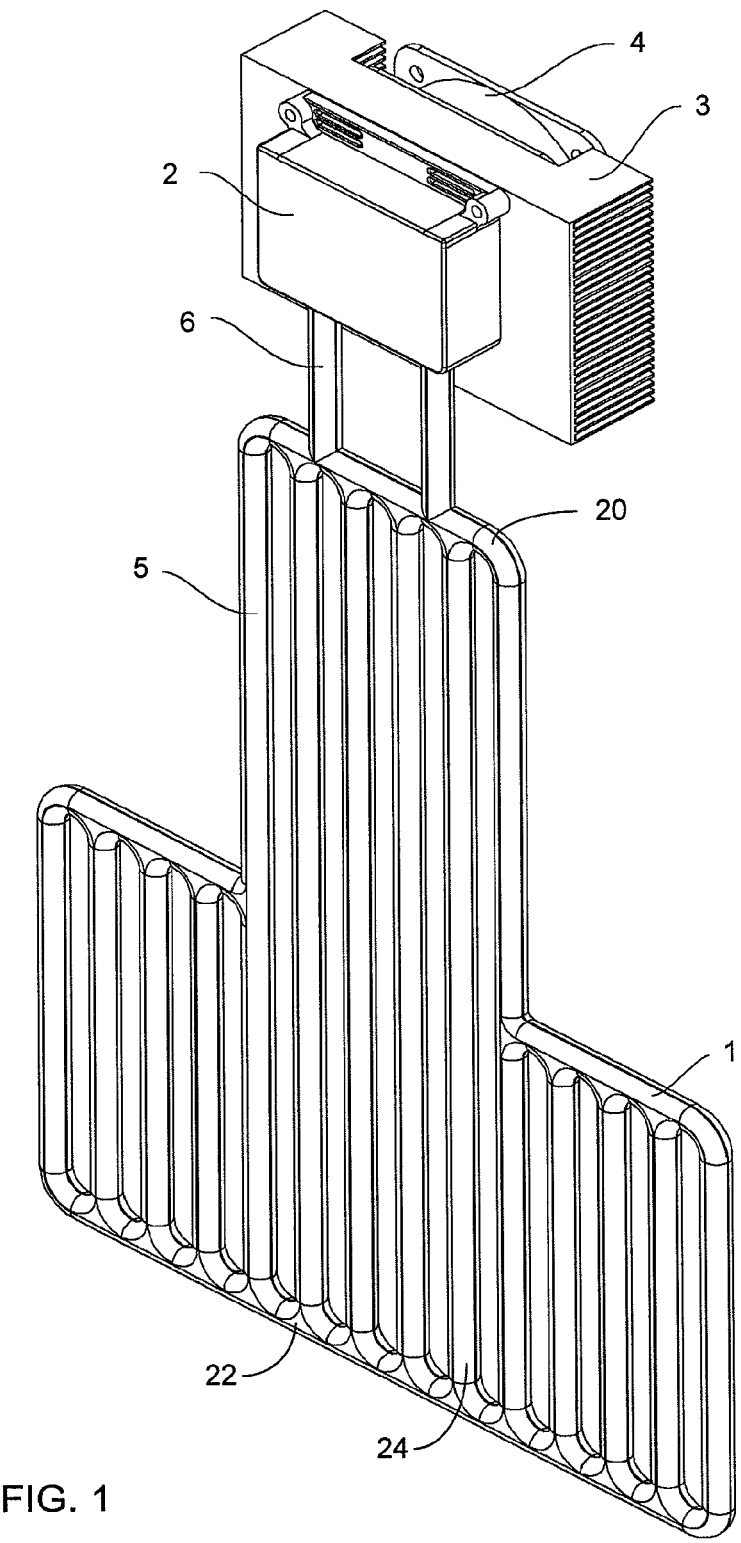
FIG. 1 is a perspective view of the preferred embodiment.

FIG. 1 depicts a perspective view of one preferred embodiment of the present invention. The bladder(1) is comprised of two sheets of PVC which are sandwiched and sealed at the edges using RF welding. Further seals within the bladder(1) are added in a vertical manner to create channels(5). The channels (5) may be disposed between a proximate manifold (20) located near a cooling unit (2), and a distal manifold (22) located on a side of the bladder (1) opposite the proximate manifold (20). This gives the bladder(1) structure and are used to guide the liquid in the bladder up and down. In this preferred embodiment the liquid in the bladder(1) is water. When the water in the bladder(1) is heated up by the person being cooled it becomes more buoyant. Because the bladder (1) has these channels(5) the water floats up with little interaction with other water molecules in the bladder(1). The present invention must be oriented so that it pitches up with the cooling unit(2) on top. This ensures that the warmed water is floating towards the cooling unit(2). In this preferred embodiment the bladder(1) has two tubes(6) connecting it to the cooling unit 2). These tubes(6) give passage for the water to move from the bladder(1) to the cooling unit(2) in a closed circuit. One tube(6) goes to the inlet of the cooling unit(2) and the other the outlet. Once inside the cooling unit(2) heat is removed from the water making it more dense and thus heavier. The now heavier water assisted by gravity flows out of the cooling unit(2) outlet, through the tube(6) and back to the bladder(1). At least one full-length channel (24) spans from the proximate manifold (20) to the distal manifold (22) in the bladder(1) to ensure that the water flows all the way down to the bottom of the bladder(1). This method of passive heat exchange based on natural convection which circulates liquid in a vertical closed-loop circuit without requiring a conventional pump is called a thermosiphon. Heat collected in the cooling unit(2) is moved via thermoelectric modules to a convection heat sink(3). A fan(4) blows ambient air across the convection heat sink(3) so heat can be expelled from the system.

Figure 2:
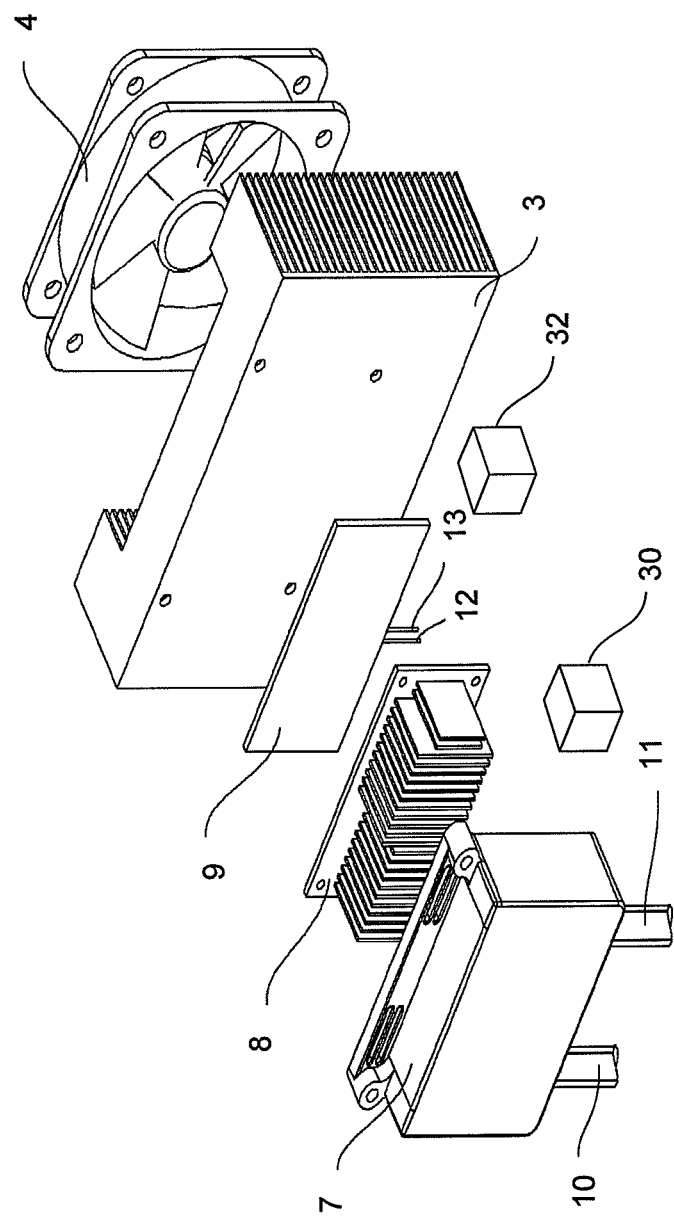
FIG. 2 is an exploded partial perspective view of the cooling unit incorporated in the present invention.

FIG. 2 is an exploded partial perspective view of the cooling unit incorporated in the present invention giving a more detailed view of the cooling unit then FIG. 1. The manifold(7) is a polycarbonate plastic shell with an inlet(10) and an outlet (11) hole at the bottom which holds the water and a conduction heat sink(8). The conduction heat sink(8) is constructed from aluminum and is sealed to the manifold(7) submersing a finned side in the water and leaving a flat side exposed. The fins absorb heat from the water and conduct it away to the flat side. The flat side of conduction heat sink(8) is pressed against one side of the thermoelectric module(9). The thermoelectric module(9) produces a temperature differential between its hot side and its cold side when electricity is applied to the modules two wire leads(12)(13). The cold side which is pressed against the conduction heat sink(8) draws in heat and pushes it to its hot side. The hot side of the thermoelectric module(9) is pressed against a convection heat sink (3) which is also made from aluminum. Heat from the thermoelectric module(9) is pushed in the convection heat sink(3) thereby raising its temperature above ambient air. A fan(4) blows ambient air across the convection heat sink(3) so heat can be expelled from the system via convection. An optional liquid flow rate regulator (30) may control the amount of liquid flowing between the bladder and the thermoelectric cooling unit. Further, an optional thermoelectric cooling unit (32) may be used to aid in keeping a temperature of the liquid to a desired level.

Figure 3:
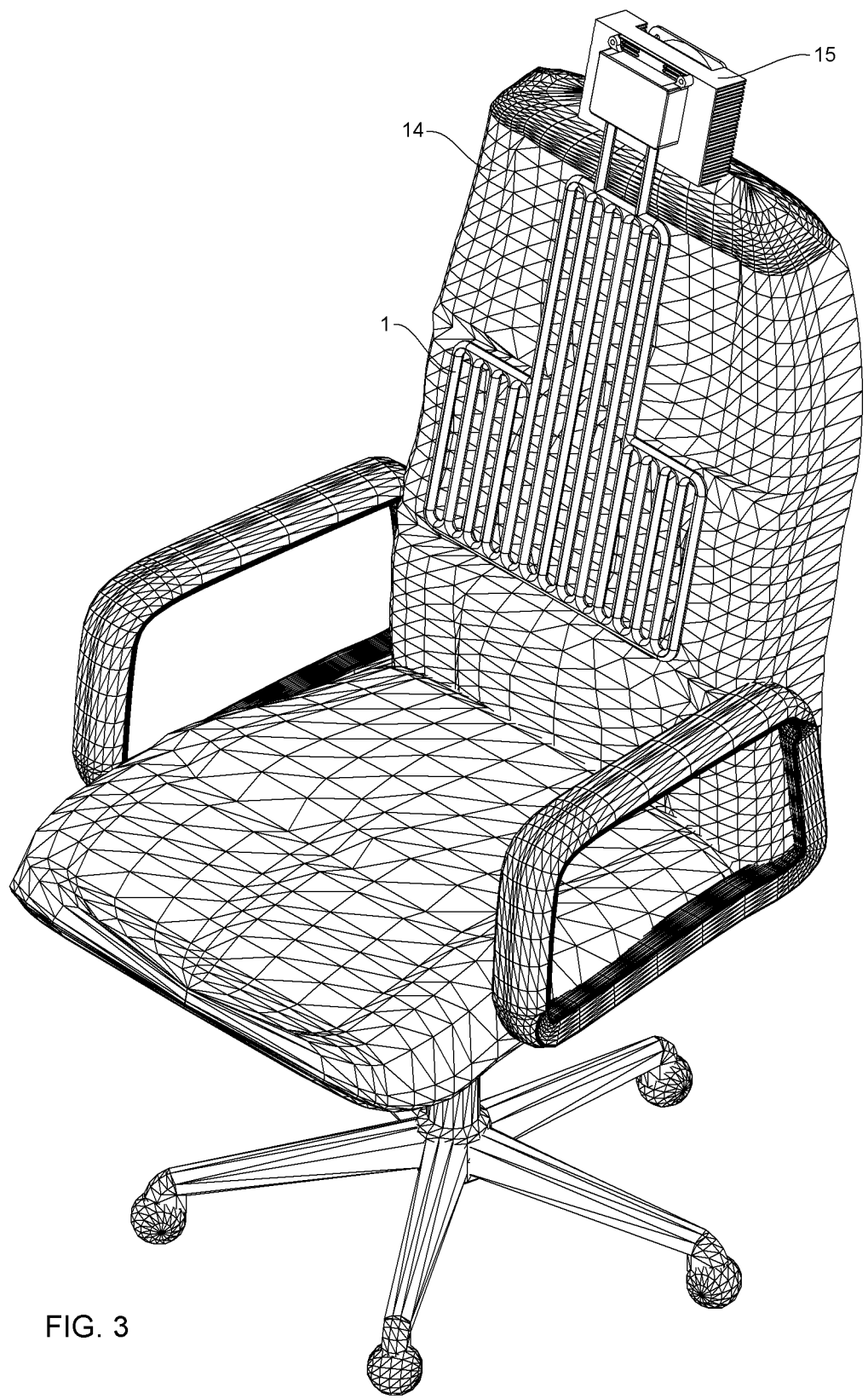
FIG. 3 is a perspective view of the preferred embodiment with an office chair.

FIG. 3 is a perspective view of the preferred embodiment with an office chair. The present invention(15) is draped over the back of an office chair(14) with the pliant bladder(1) covering the back rest of the chair. When a person occupies the office chair(14) the bladder(1) will be between the persons back and the chair back. Body heat from the person which would normally be insulated by the chair is removed by the present invention(15).

What is claimed is:

1. A passive flow therapeutic cooling system, comprising:
    a cooling unit comprising a thermoelectric module, wherein when electricity is applied the thermoelectric module produces a relatively cool first surface and relatively warm second surface; and
    a bladder comprising a plurality of channels in fluid communication with the cooling unit,
    wherein the cooling unit and the plurality of cooling channels form at least part of a cooling circuit,
    wherein when the thermoelectric module is disposed at a higher elevation than the bladder, when the bladder abuts a heat source, and when the cooling circuit comprises a cooling fluid comprising a boiling point above a temperature of the heat source and a freezing point below an ambient temperature, the cooling system forms a thermosyphon, and
    wherein in the cooling unit the first surface of the thermoelectric module draws heat from the cooling fluid, effective to cool the heat source.

2. The passive flow therapeutic cooling system of claim 1, wherein the bladder comprises a pliant polymeric material and thereby effective to conform to a contour of various heat sources.

3. The passive flow therapeutic cooling system of claim 1, wherein the plurality of channels are parallel to each other.

4. The passive flow therapeutic cooling system of claim 1, wherein the bladder further comprises a distal manifold at an end opposite the cooling unit, and wherein at least one of the plurality of channels is in direct fluid communication with the distal manifold and is effective to direct cooled cooling fluid from the cooling unit directly to the distal manifold.

5. The passive flow therapeutic cooling system of claim 4, wherein the bladder further comprises a proximate manifold directly connected to a plurality of tubes and the at least one of the plurality of channels, wherein the plurality of tubes provide fluid communication between the cooling unit manifold.

6. The passive flow therapeutic cooling system of claim 1, wherein the bladder further comprises a pliant material configured to form the plurality of channels.

7. The passive flow therapeutic cooling system of claim 1, wherein the bladder comprises a planar shape when unflexed.

8. The passive flow therapeutic cooling system of claim 1, wherein the bladder comprises polyvinylchloride.

9. The passive flow therapeutic cooling system of claim 1, comprising the cooling fluid.

10. The passive flow therapeutic cooling system of claim 9, wherein the cooling fluid comprises water.

11. The passive flow therapeutic cooling system of claim 1, wherein the cooling unit further comprises a temperature regulating electric control effective to produce a desired temperature in the bladder.

12. The passive flow therapeutic cooling system of claim 1, wherein
    the cooling unit further comprises a liquid flow rate regulator effective to produce a desired temperature in the bladder.

13. A passive flow therapeutic cooling system, comprising:
    a cooling unit comprising a thermoelectric module, wherein the thermoelectric module utilizes the Peltier effect to transfer heat from one side of the thermoelectric module to another side of the thermoelectric module;
    a bladder comprising a plurality of cooling channels;

a cooling fluid comprising a boiling point above a temperature of a heat source and a freezing point below an ambient temperature;

wherein, when in an operating position where the thermoelectric module is elevated above the bladder and the bladder is adjacent a heat source, the cooling fluid absorbs heat from the heat source, expands, and flows upward through at least one of the cooling channels toward the cooling unit, and wherein the cooling unit cools the heated cooling fluid through the Peltier effect, and wherein the cooled cooling fluid flows downward through at least one of the cooling channels.

14. The passive flow therapeutic cooling system of claim 13, wherein the bladder comprises a pliant material configured to form the cooling channels.

15. The passive flow therapeutic cooling system of claim 13, wherein the bladder comprises a proximate manifold disposed at an end proximate the cooling unit and a distal manifold disposed at an end opposite the proximate manifold, and wherein at least one of the plurality of cooling channels provides direct fluid communication between the manifolds.

16. The passive flow therapeutic cooling system of claim 13, wherein the bladder comprises a planar shape.

17. The passive flow therapeutic cooling system of claim 13, wherein the cooling fluid comprises water.

18. The passive flow therapeutic cooling system of claim 13, further comprising a temperature regulating electric control or a liquid flow rate regulator.

19. A passive flow therapeutic cooling system, comprising:
a cooling unit comprising a thermoelectric module, wherein the thermoelectric module utilizes the Peltier effect to transfer heat from one side of the thermoelectric module to another side of the thermoelectric module;

a bladder comprising a proximate manifold proximate the cooling unit, a distal manifold opposite the cooling unit, and a plurality of parallel cooling channels spanning the manifolds, the manifolds and plurality of cooling channels forming a flexible planar array;

a cooling liquid that remains liquid at a temperature of a heat source and at an ambient temperature;

wherein, when in an operating position where the thermoelectric module is elevated above the bladder and the bladder is adjacent a heat source, the cooling fluid absorbs heat from the heat source, expands, and flows upward through at least one of the cooling channels toward the cooling unit, and wherein the cooling unit cools the heated cooling fluid through the Peltier effect, and wherein the cooled cooling fluid flows downward through at least one of the cooling channels to the distal manifold.

20. The passive flow therapeutic cooling system of claim 1, further comprising a heat sink in thermal communication with the second surface of the thermoelectric module and a cooling fan configured to cool the heat sink, wherein the heat sink is configured to cool the second surface such that the temperature of the first surface is below the ambient temperature.

* * * * *